US00PP15089P2

(12) United States Plant Patent
Carruth

(10) Patent No.: US PP15,089 P2
(45) Date of Patent: Aug. 17, 2004

(54) CLIMBING ROSE PLANT NAMED 'WEKAMARSODO'

(50) Latin Name: *Rosa hybrida*
Varietal Denomination: WEKamarsodo

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 10/720,612

(22) Filed: Nov. 20, 2003

(51) Int. Cl.[7] ..... A01H 5/00
(52) U.S. Cl. ..... Plt./115
(58) Field of Search ..... Plt./115, 109

*Primary Examiner*—Anne Marie Grunberg
*Assistant Examiner*—June Hwu
(74) *Attorney, Agent, or Firm*—Christie, Parker & Hale, LLP

(57) ABSTRACT

A new variety of Climbing rose suitable for garden decoration, having flowers of even medium red coloration.

1 Drawing Sheet

Classification: The present invention relates to a new *Rosa hybrida* plant.

Variety denomination: The new plant has the varietal denomination 'WEKamarsodo'.

BACKGROUND OF THE INVENTION

This invention relates to a new and distinct variety of Climbing Rose. It has as its seed parent an undisseminated, unpatented seedling of my creation. It has as its pollen parent another undisseminated, unpatented seedling of my creation.

SUMMARY OF THE INVENTION

Among the features which distinguish the new variety from other presently available and commercial rose cultivars known to the inventor are the following combination of characteristics: its excellent color stability throughout the life of the flower, its red suffusion on the upper side of the rachis, its numerous stipitate glands on the edge of the stipule and its abundant prickles. The plant has a spreading climbing growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKamarsodo' may be asexually propagated by cuttings, budding and grafting. The budding and grafting successfully occurred on the plant/rootstock *Rosa hybrida* cv. 'Dr. Huey'.

COMPARISON WITH PARENTS

The new rose may be distinguished from its seed parent, an undisseminated, unpatented seedling of my creation by the following combination of characteristics: whereas 'WEKamarsodo' bears medium sized flowers (about 6.8 to about 8.5 cm. in diameter) with double petalage (about 27 to 32), the seed parent bears significantly larger flowers (about 9 to about 11 cm. in diameter) with lesser petalage (about 12 to 17). The new variety bears its flowers in large clusters, whereas the seed parent bears its flowers in significantly smaller clusters.

The new variety may be distinguished from its pollen parent, an undisseminated, unpatented seedling of my creation by the following combination of characteristics: whereas 'WEKamarsodo' bears flowers of even medium red coloration with double petalage (about 27 to 32 petals), the undisseminated seedling bears flowers of deep pink coloration with significantly heavier petalage (about 35 to 42 petals). The pollen parent bears foliage with a matte finish, whereas the new variety bears foliage with a moderately glossy finish.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors is Upland, Calif. in the month of October. Phenotypic expression may vary with environmental, cultural and climatic conditions, as well as differences in conditions of light and soil.

FLOWER

The new variety usually bears its flowers in clusters of five to eight or more per stem. Flowers are borne in regular rounded clusters on strong medium to long stems (about 50 to about 170 cm.). Outdoors, the plant blooms abundantly and nearly continuously during the growing season. The flowers have a moderate tea fragrance.

BUD

The peduncle is about 3.2 to about 3.9 cm. in length, of average caliper (about 0.2 to about 0.4 cm. in diameter), and usually erect to somewhat stiff. It is rough, with many stipitate glands, few hairs and many small prickles. Peduncle color is between 144A and 146D often heavily suffused, especially on the side exposed to the sun, with between 187B and 183B.

Before the calyx breaks, the bud is about 1.1 to about 1.7 cm. in diameter at the widest point, about 1.2 to about 1.7 cm. in length, and moderately pointed to somewhat ovoid in shape. The surface of the bud bears few foliaceous appendages and numerous stipitate glands, usually with slender mostly entire but sometimes slightly cut foliaceous parts extending beyond the tip of the bud about ½ or more of its length. Bud color is between 137C and 146B sometimes heavily suffused, especially on the side exposed to the sun, with between 187B and 187A.

The sepals are about 2.2 to about 2.8 cm. in length and about 0.8 to about 1.1 cm. in width at the widest point. The outer surface color of the sepal is between 137C and 146B sometimes heavily suffused, especially on the side exposed to the sun, with between 187B and 187A. The inner surface color of the sepal is between 138B and 137B and covered with fine wooly tomentum; sepal margins are lined with many stipitate glands and hairs.

As the petals open (after the calyx breaks), the bud is about 2.1 to about 2.6 cm. in diameter at the widest point, about 2.3 to about 2.8 cm. in length, and moderately ovoid to somewhat globular in form. The color of the under surfaces of the newly opened petals is between 53A and 187A. At the point where the petal attaches, there is a small zone of between 4C and 3D. The color of the upper surfaces of the newly opened petals is between 53A and 187A. At the point where the petal attaches, there is a moderately small zone of between 7C and 6B.

BLOOM

When fully open, the bloom ranges from about 6.8 to about 8.5 cm. in diameter. Petalage is double with about 27 to 32 petals and about 1 to 4 petaloids irregularly arranged. When partially open, the bloom form is very globular, and the petals are somewhat tightly spiraled to slightly undulated with petal edges moderately reflexed outward. When fully open, the bloom form is moderately cupped, and the petals are loosely cupped to moderately undulated with petal edges moderately reflexed outward.

PETALS

The substance of the petals is somewhat heavy to moderately leathery and of medium thickness, with upper surfaces moderately satiny to somewhat velvety and under surfaces slightly shiny to matte. The outer petals are moderately obovate to somewhat rounded in shape with rounded apices and sometimes slightly notched with one notch. The inner petals are moderately obovate in shape with rounded apices and sometimes slightly notched with one notch. The petals are about 3.6 to about 4.5 cm. in length and about 3.2 to about 4.2 cm. in width at the widest point. Petal margins are entire.

NEWLY OPENED FLOWER

The under surface color of the outer, intermediate and inner petals is between 53A and 53C. At the point where the petal attaches, there is a small zone of between 1D and 2D. The upper surface color of the outer, intermediate and inner petals is between 53A and 53B. At the point where the petal attaches, there is a moderately small zone of between 4C and 5D.

The general tonality of the newly opened flower is between 53A and 53B.

THREE-DAY-OLD FLOWER

The under surface color of the outer, intermediate and inner petals is between 61C and 64C at the base of the petal that gradually suffuses to between 53A and 53C from the center to the very tip of the petal. At the point where the petal attaches, there is a small zone of between 155B and 2D. The upper surface color of the outer, intermediate and inner petals is between 61C and 64C at the base of the petal that gradually suffuses to between 53A and 53B from the center to the very tip of the petal. At the point where the petal attaches, there is a moderately small zone of between 155B and 4D.

The general tonality of the three-day-old flower is between 61C and 64C at the base of the petal that gradually suffuses to between 53A and 53B from the center to the very tip of the petal.

On the spent bloom, the petals usually drop off cleanly.

In October in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are many in number (average about 165) and are arranged regularly about the pistils; a few are mixed with petaloids. The filaments are of medium to somewhat long length (about 0.5 to about 0.9 cm.), most with anthers. Filaments are between 6B and 5B at the base suffusing to between 35B and 33C in color near the top. The anthers are somewhat large for the class and all open approximately at the same time. Anther color is between 24B and 26D when immature and between 200A and 164B at maturity. Pollen is abundant.

FEMALE REPRODUCTIVE ORGANS

Pistils vary in number (average about 105). The styles are moderately uneven, somewhat long in length (about 0.3 to about 0.9 cm.), thin in caliper, and very loosely separated. Stigma color is between 5D and 8C. Style color is between 2D and 1D often heavily suffused near the top with between 53B and 53C. Ovaries are usually all enclosed in the calyx.

Hips are average in length (about 1.9 to about 2.6 cm.), moderately globular in form, and between 33A and 32A in color when ripe. The hip surface is smooth with few stipitate glands and thick fleshy walls. The sepals are moderately permanent, and usually straight in shape. The seeds are irregularly rounded, smooth in texture, approximately 13 to about 24 per hip, about 0.4 to about 0.6 cm. in diameter at the widest point and between 161C and 164C in color.

FOLIAGE

The compound leaves are usually comprised of three to seven or more leaflets and are borne abundantly. The seven-leaflet leaves are about 11.9 to about 19.0 cm. in length and about 8.1 to about 12.8 cm. in width at the widest point, somewhat thin to leathery in texture, and moderately glossy in finish. The terminal leaflets are about 4.6 to about 7.3 cm.

in length and about 2.9 to about 4.8 cm. in width at the widest point, shaped ovate to somewhat oval with acute apices and moderately rounded to somewhat acute bases. Their margins are usually simply serrate.

The upper surface color of the mature leaf is between 147A and 131A. The under surface color of the mature leaf is between 147B and 136B. The upper surface color of the young leaf is between 147B and 131A, usually heavily suffused with between 187A and 183A. The under surface color of the young leaf is between 147B and 146B, usually heavily suffused with between 187B and 183B.

The rachis is moderately light in caliper and rough. The upper side is moderately grooved with few hairs and many stipitate glands on the edges of the grooves. The under side of the rachis is rough with some stipitate glands and few small prickles. The rachis color is between 144A and 146B sometimes heavily suffused, especially on the young leaves, with between 187A and 183A.

The stipules are about 1.6 to about 2.4 cm. in length and moderately wide (about 0.6 to about 1.1 cm.) with somewhat short straight points that usually turn out at an angle of more than 45 degrees and sometimes recurve toward the stem. The stipules are edged with numerous stipitate glands. The stipules color is between 146C and 137A sometimes moderately suffused, especially on the young leaves, with between 187C and 183C.

The petiole is about 0.5 to about 1.1 cm. in length and about 0.15 to about 0.2 cm in diameter at the widest point. The petiole color is between 144A and 146B sometimes heavily suffused, especially on the young leaves, with between 187A and 183A.

The plant displays an above average degree of resistance to powdery mildew and rust as compared to other commercial varieties grown under comparable conditions in Upland, Calif. The plant's winter hardiness and drought/heat tolerance are yet to be determined.

GROWTH

The plant has a spreading climbing growing habit with canes about 250 to about 380 cm. in length. It displays vigorous growth and the canes are of medium to somewhat heavy caliper for the class.

The color of the major stems is between 146B and152A. They bear many large prickles that are about 0.5 to about 0.7 cm. in length. The large prickles are slightly hooked downward with a medium length oval base; prickle color is between 199B and 166A. The major stem bears many small prickles of similar shape and coloration.

The color of the branches is between 146A and 146C. They bear several large prickles which are about 0.7 to about 1.1 cm. in length and of similar shape to the large prickles on the major stems; prickle color is between 165B and 164C. The branches bear several small prickles of similar shape and coloration.

The color of the new shoots is between 144B and 146C sometimes lightly suffused with between 187C and 183C. They bear many large prickles which are of similar size and shape to the large prickles on the branches; prickle color is between 145A and 150B often moderately suffused with between 187D and 184B. The shoots bear many small prickles of similar shape and coloration.

I claim:

1. A new and distinct Climbing rose plant of the variety substantially as described and illustrated herein.

* * * * *

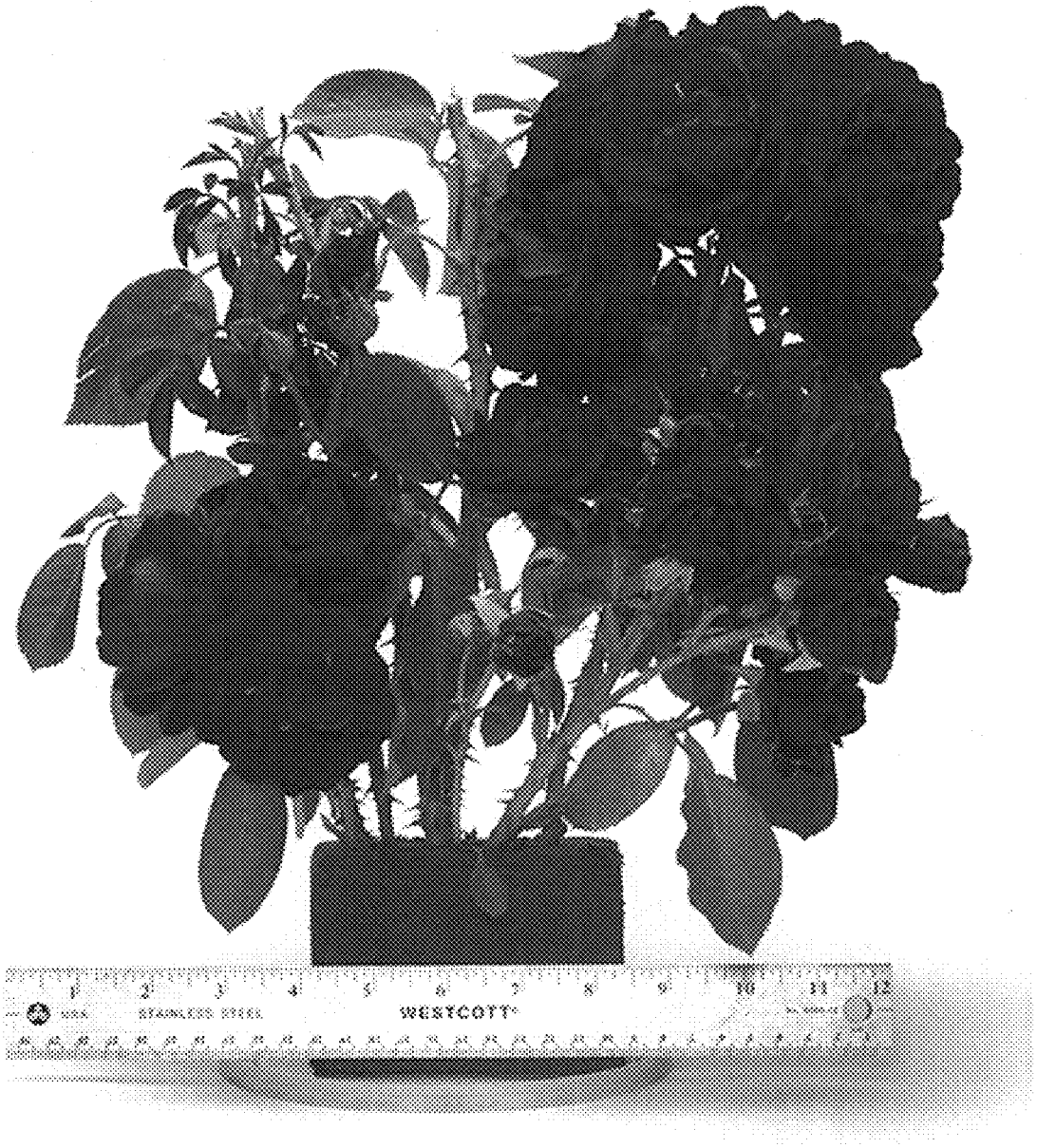
STAINLESS STEEL
WESTCOTT